United States Patent [19]
Imai et al.

[11] Patent Number: 5,882,863
[45] Date of Patent: Mar. 16, 1999

[54] METHOD OF MEASURING NUCLEIC ACIDS AND REAGENT USED THEREFOR

[75] Inventors: Kyoko Imai; Junko Momose; Yasushi Nomura, all of Katsuta, Japan

[73] Assignee: Hitachi, Ltd., Tokyo, Japan

[21] Appl. No.: 658,398

[22] Filed: Jun. 5, 1996

Related U.S. Application Data

[63] Continuation of Ser. No. 199,030, Feb. 18, 1994, abandoned.

[30] Foreign Application Priority Data

Feb. 19, 1993 [JP] Japan ..................................... 5-030589

[51] Int. Cl.$^6$ ............................... C12Q 1/70; C12Q 1/68; C07H 21/02; G01H 33/544
[52] U.S. Cl. ................................... 435/6; 435/5; 436/528; 436/531; 436/532; 436/534; 536/23.1; 536/24.3
[58] Field of Search ............................ 435/6, 5, 7.1, 7.9; 536/23.1, 24.3; 436/528, 531, 532, 533, 534

[56] References Cited

U.S. PATENT DOCUMENTS

| | | | |
|---|---|---|---|
| 4,775,619 | 10/1988 | Urdea ........................................... | 435/6 |
| 5,112,736 | 5/1992 | Caldwell et al. ........................... | 435/6 |
| 5,210,015 | 5/1993 | Gelfand ....................................... | 435/6 |
| 5,308,990 | 5/1994 | Takahashi et al. .................. | 250/459.1 |
| 5,326,692 | 7/1994 | Brinkley et al. ........................... | 435/6 |
| 5,543,292 | 8/1996 | Imai et al. .................................. | 435/6 |
| 5,573,909 | 11/1996 | Singer et al. .............................. | 435/6 |

OTHER PUBLICATIONS

Southern Detection of specific sequences among DNA fragments separated by gel electrophoresis J. Mol. Boil. vol. 98, pp. 503–517 1975.

Meinkoth et al. Hybridization of nucleic acids immobilized on solid supports. Anal. Biochem. vol. 138, pp. 267–284 1884.

Matthews et al. Analytical strategies for the use of DNA probes. Analytical Biochemistry. vol. 169, pp. 1–25 1988.

*Primary Examiner*—Kenneth R. Horlick
*Assistant Examiner*—Joyce Tung
*Attorney, Agent, or Firm*—Antonelli, Terry, Stout & Kraus, LLP

[57] ABSTRACT

A nucleic acid sample is mixed with a nucleotide reagent under hybridizing conditions. The nucleotide reagent contains nucleotides each combined at 3'- and 5'-terminals thereof with particles. After cleaving double strands of hybridization products, at least ones of particles separated from each other by the cleaving and particles held in the unreacted reagent and subjected to no cleavage are detected for measuring nucleic acids in the sample. Since the particles separated from each other by the cleaving and the particles held in the unreacted reagent and subjected to no cleavage are different in size of particle masses from each other, these two groups of particles can be discriminated and detected. Therefore, a labeling substance in the unreacted reagent is no longer required to be washed and separated, enabling nucleic acids to be quickly measured with high sensitivity.

19 Claims, 12 Drawing Sheets

NON-FLUORESCENT PARTICLE

FLUORESCENT PARTICLE

NON-FLUORESCENT PARTICLE

FIG. 13

TABLE 1

| SAMPLE NO. | NUMBER OF FREE PARTICLES DETECTED |
|---|---|
| 1 | 4 2 1 1 3 2 5 |
| 2 | 2 3 0 1 8 3 3 |
| 3 | 1 5 1 8 2 2 6 5 |
| 4 | 3 5 0 |
| 5 | 1 2 9 |

FIG. 14

TABLE 2

| SAMPLE NO. | NUMBER OF FREE PARTICLES DETECTED |
|---|---|
| 1 | 1 9 5 2 3 5 6 4 2 |
| 2 | 6 3 5 2 6 5 2 0 |
| 3 | 5 2 8 5 2 6 3 |
| 4 | 1 5 6 8 2 1 1 3 |
| 5 | 6 |

METHOD OF MEASURING NUCLEIC ACIDS AND REAGENT USED THEREFOR

This application is a Continuation application of Ser. No. 08/199,030 filed Feb. 18, 1994, now abandoned.

FIELD OF THE INVENTION

The present invention relates to a method of measuring nucleic acids and a reagent used therefor, and more particularly to a method of measuring nucleic acids in which a nucleotide combined with particles as solid phase substances is used as a nucleic acid probe, and a reagent for use in the measuring method.

BACKGROUND OF THE INVENTION

Detection and identification of pathogenic microorganisms are indispensable for diagnoses of infectious diseases. However, detection and identification of a microorganism responsible for an infectious disease by cultivation is so time consuming that it is often not available for practical diagnosis and treatment of the disease. Therefore, diagnoses using immunological inspection methods have become more popular. In immunological inspection methods, proteins on the cell surface layers of microorganisms or antigenic substances produced in large amount during the process of proliferation are mainly detected, but these proteins, etc. are not always related to the microorganisms responsible for the diseases. This is because measuring the increased antibody titer in the serum of a patient for a specific pathogenic microorganism or the specific antigen thereof is measurement of a response to the infectious disease and is not confirmation of the microorganism per se.

Recently, investigation of the existence of a specified base sequence in a nucleic acid sample using a hybridization technique for nucleic acids has made it possible to specify a microorganism responsible for an infectious disease and diagnosis of the infectious disease before crisis. Thus, a method using a DNA probe for microorganism detection has been practiced. In this method, a single-stranded DNA having a base sequence complementary to the base sequence of a nucleic acid which is contained in a sample to be detected (the single-stranded DNA is referred to as "DNA probe") is utilized as a specifically reactive reagent. The existence of objective pathogenic bacteria can be judged by investigating the existence, in a sample, of a base sequence complementary to the base sequence of the DNA probe. Various practical methods have been proposed in, e.g., (1) Nippon Rinsho (Clinical Medicine in Japan), Vol. 47, 737–754, (1989), (2) E. M. Southern, "Detection of Specific Sequences Among DNA Fragments Separated by Gel Electrophoresis", *J. Mol. Biol.*, 98, pp503–517, (1975), and (3) J. Meinkoth & G. Wahl, "Hybridization of Nucleic Acids Immobilized on Solid Supports", Analytical Biochemistry, 138, pp267–284, (1984). One example of a method using the DNA probe is called dot hybridization. This method comprises attaching a single-stranded DNA (an SS-DNA) obtained by denaturation of a sample to a solid phase, allowing a radioisotope-labeled SS-DNA to act on the solid phase to form a hybrid between the labeled SS-DNA and the SS-DNA attached to the solid phase, removing the unreacted labeled SS-DNA, and measuring a radiation emitted from the solid phase (hereinafter referred to as "first prior art technique").

As a modification of the above method, there is a method of sandwich hybridization. This method makes it possible to reduce the background due to adsorption and hence is effective particularly when an impure sample is used. In this method, at least two DNA fragments derived from a target nucleic acid to be detected are used. One of the DNA fragments is attached to a solid phase and used as a capturing reagent. The other fragment is labeled as a reagent for detection and added to a solution containing the solid phase to which the capturing reagent is attached, together with a solubilized sample in a hybridizing solution. Then, the reagent for detection which has been bound to the solid phase by hybridization and the unreacted reagent for detection are separated from each other. When a base sequence homologous with both the reagents exists in the sample, the sequence is hybridized with both the capturing reagent and the reagent for detection. Whether the sequence has been hybridized or not can be known by measuring the label in the reagent for detection which has been bound to the capturing reagent in the solid phase through the sample. (This method will hereinafter be referred to as "second prior art technique".)

Further, JP, B, 3-78120 proposes a method using a restriction enzyme. The proposed method comprises bringing, in a solution, a single-stranded polynucleotide to be measured into contact with a solid phase combined with a single-stranded polynucleotide to which a labeling substance has been attached and which is capable of reacting with the single-stranded polynucleotide to be measured to form a double-stranded polynucleotide, thereby forming the double-stranded polynucleotide, allowing a restriction enzyme to act on the formed double-stranded polynucleotide to cleave this double-stranded polynucleotide, and measuring the labeling substance in the solution or solid phase (hereinafter referred to as "third prior art technique").

The above prior art methods however have the following problems.

The first and second prior art techniques are problematic, particularly when the amount of a nucleic acid to be detected is small, because the nucleic acid to be detected in the sample must finally be bound to the solid phase in either technique. Also, they require a large number of steps for completing measurement and, particularly, require the operation of separating the unreacted reagent in the solution for measuring the labeling substance in the reagent which has been hybridized with the nucleic acid to be detected. Further, immobilization of a sample slowly progresses because of a solid/liquid reaction and takes a long time. Thus, the first and second prior art technique are disadvantageous from the viewpoint of labor required for operations and time required for measurement.

In the third prior art technique, since a reagent capable of being treated beforehand is bound to a solid phase, immobilization of a sample is not necessary and the problems with the first and second prior arts are partly solved. However, the third prior art technique is disadvantageous in that a labeling substance is detected based on its concentration and hence detection sensitivity is not sufficient. For example, when an enzyme is used as the labeling substance, reliability of the measured values at low concentrations is poor because of not only limits in chemical amplification due to the enzyme reaction as high as about 104 at the maximum, but also influences of decomposition of the substrate, etc. The amplification due to the enzyme reaction is unstable because it is different depending on reaction conditions and is easily affected by coexisting substances. As a method of compensating for such a drawback, there is a method of amplifying DNA fragments of a sample. From the viewpoint of practical use, however, this method has problems of requiring a long time and causing contamination of a sample.

Additionally, in the third prior art technique, before cleaving each double strand formed by the reaction, completion of measurement also requires separation, in the solution, of the labeling substance which is in the unreacted reagent existing free in the solution and the labeling substance which has been attached to the solid phase by the reaction.

SUMMARY OF THE INVENTION

An object of the present invention is to solve the above-described problems, and to provide a method of measuring nucleic acids which is capable of quick treatment, has good detection sensitivity, and a reagent for use in the measuring method.

Another object of the present invention is to provide a method of measuring nucleic acids in which an unreacted labeling reagent is no longer required to be washed and separated, and a reagent for use in the measuring method.

As a result of conducting intensive studies aiming to overcome the problems discussed above, the inventors have accomplished the present invention based on a finding that the above objects can be achieved by using, as a reagent, a nucleotide combined at 3'- and 5'-terminals thereof with particles.

More specifically, the method of measuring nucleic acids according to a first aspect of the present invention comprises the steps of using, as a reagent, nucleotides each combined at 3'- and 5'-terminals thereof, respectively, with first and second particles, allowing said reagent to react with a sample for forming double-stranded nucleotides, cleaving a double strand of each of said double-stranded nucleotides, discriminating and detecting the first and second particles separated from each other by said cleaving and the first and second particles held in the unreacted reagent and subjected to no cleavage, counting the number of the particles in at least one group, and measuring an objective component in said sample based on said counted particle number.

The method of measuring nucleic acids according to a second aspect of the present invention comprises the steps of using, as a reagent, nucleotides each combined at 3'- and 5'-terminals thereof with labeling substances as a binder (a binder having a binding moiety) and first and second particles combined with labeling substances (binder) being capable of respectively specifically binding to said binders, allowing said reagent to react with a sample for binding said first and second particles to the 3'- and 5'-terminals of the nucleotides, respectively, and also forming double-stranded nucleotides, cleaving a double strand of each of said double-stranded nucleotides, discriminating and detecting the first and second particles separated from each other by said cleaving and the first and second particles held in the unreacted reagent and not subjected to cleavage, counting the number of the particles in at least one group, and measuring an objective component in said sample based on said counted particle number.

The method of measuring nucleic acids according to a third aspect of the present invention comprises the steps of using, as a reagent, nucleotides each combined at one of 3'- and 5'-terminals thereof with a labeling substance as a binder (binder having a binding moiety) and at the other terminal with a first particle, and second particles each combined with a labeling substance (binder) being capable of specifically binding to said labeling substance (binder), allowing said reagent to react with a sample for binding said first and second particles to the 3'- and 5'-terminals of the nucleotides, respectively, and also forming double-stranded nucleotides, cleaving a double strand of each of said double-stranded nucleotides, discriminating and detecting the first and second particles separated from each other by said cleaving and the first and second particles held in the unreacted reagent and not subjected to cleavage, counting the number of the particles in at least one group, and measuring an objective component in said sample based on said counted particle number.

In the method of measuring nucleic acids according to any one of the first to third aspects, preferably, a particle having a label for detection is used as at least one of said first particle and said second particle. Also preferably, a light emitting particle is used as at least one of said first particle and said second particle. The term "light emitting particle" used here means a particle capable of eventually radiating light. Desirably, a fluorescent particle is used. A particle having no label for detection may be used as at least one of said first particle and said second particle. Alternatively, a magnetic particle may be used as at least one of said first particle and said second particle.

Further, in the method of measuring nucleic acids according to any one of the first to third aspects, an enzyme is preferably used to cleave the double strand of said double-stranded nucleotide.

The method of measuring nucleic acids according to a fourth aspect of the present invention comprises the steps of using, as a reagent, nucleotides each combined at 3'- and 5'-terminals thereof with light emitting particles, allowing said reagent to react with a sample for forming double-stranded nucleotides, cleaving a double strand of each of said double-stranded nucleotides, discriminating and detecting the light emitting particles separated from each other by said cleaving and the light emitting particles held in the unreacted reagent and not subjected to cleavage, counting the number of the light emitting particles in at least one group, and measuring an objective component in said sample based on said counted particle number.

The method of measuring nucleic acids according to a fifth aspect of the present invention comprises the steps of using, as a reagent, nucleotides each combined at one of 3'- and 5'-terminals thereof with a light emitting particle and at the other terminal with a particle having no label for detection, allowing said reagent to react with a sample for forming double-stranded nucleotides, cleaving a double strand of each of said double-stranded nucleotides, discriminating and detecting the particles separated from each other by said cleaving and the particles held in the unreacted reagent and not subjected to cleavage, counting the number of the particles in at least one group, and measuring an objective component in said sample based on said counted particle number.

The method of measuring nucleic acids according to a sixth aspect of the present invention comprises the steps of using, as a reagent, nucleotides each combined at 3'- and 5'-terminals thereof with respective particles having different particle sizes and having no labels for detection, allowing said reagent to react with a sample for forming double-stranded nucleotides, cleaving a double strand of each of said double-stranded nucleotides, discriminating and detecting the small- and large-size particles separated from each other by said cleaving and the particles held in the unreacted reagent and not subjected to cleavage, counting the number of the particles in at least one group, and measuring an objective component in said sample based on said counted particle number.

The method of measuring nucleic acids according to a seventh aspect of the present invention comprises the steps of using, as a reagent, nucleotides each combined at one of 3'- and 5'-terminals thereof with a particle having a label for detection and at the other terminal with a magnetic particle, allowing said reagent to react with a sample for forming double-stranded nucleotides, cleaving a double strand of each of said double-stranded nucleotides, attracting said each magnetic particle by a magnet, detecting the labeling particles liberated by said cleaving, counting the number of said liberated particles, and measuring an objective component in said sample based on said counted particle number.

The method of measuring nucleic acids according to an eighth aspect of the present invention comprises the steps of using, as a reagent, nucleotides each combined at one of 3'- and 5'-terminals thereof with a particle having no label for detection and at the other terminal with a magnetic particle, allowing said reagent to react with a sample for forming double-stranded nucleotides, cleaving a double strand of each of said double-stranded nucleotides, attracting said each magnetic particle by a magnet, detecting the non-labeling particles liberated by said cleaving, counting the number of said liberated particles, and measuring an objective component in said sample based on said counted particle number.

The method of measuring nucleic acids according to a ninth aspect of the present invention comprises the steps of using, as a reagent, nucleotides each combined at 3'- and 5'-terminals thereof with particles, these particles being combined respectively with other particles to produce particle aggregates in the matrix form, allowing said reagent to react with a sample for forming double-stranded nucleotides, cleaving a double strand of each of said double-stranded nucleotides, discriminating and detecting the particle aggregates in the matrix form separated from each other by said cleaving and the particle aggregates in the matrix form held in the unreacted reagent and not subjected to cleavage, counting the number of the particles in at least one group, and measuring an objective component in said sample based on said counted particle number.

On the other hand, the reagent used for measuring nucleic acids according to a first aspect of the present invention contains nucleotides each combined at 3'- and 5'-terminals thereof respectively with first and second particles.

The reagent used for measuring nucleic acids according to a second aspect of the present invention contains nucleotides each combined at 3'- and 5'-terminals thereof with labeling substances as a binder (binder having a binding moiety), and first and second particles combined with labeling substances (a binder) being capable of respectively specifically binding to said labeling substances (binder).

The reagent used for measuring nucleic acids according to a third aspect of the present invention contains nucleotides each combined at one of 3'- and 5'-terminals thereof with a labeling substance as a binder (binder) and at the other terminal with a first particle, and second particles each combined with a labeling substance (binder) being capable of specifically binding to said labeling substance (binder).

In the reagent used for measuring nucleic acids according to any one of the first to third aspects, preferably, at least one of said first particle and said second particle is a particle having a label for detection. Also preferably, at least one of said first particle and said second particle is a light emitting particle, desirably a fluorescent particle. At least one of said first particle and said second particle may be a particle having no label for detection. Alternatively, at least one of said first particle and said second particle may be a magnetic particle.

Moreover, the reagent used for measuring nucleic acids according to any one of the first to third aspects preferably further contains an enzyme for cleaving a double strand of each of double-stranded nucleotides formed by reaction between said nucleotides and a sample.

The reagent used for measuring nucleic acids according to a fourth aspect of the present invention contains nucleotides each combined at 3'- and 5'-terminals thereof with light emitting particles.

The reagent used for measuring nucleic acids according to a fifth aspect of the present invention contains nucleotides each combined at one of 3'- and 5'-terminals thereof with a light emitting particle and at the other terminal with a particle having no label for detection.

The reagent used for measuring nucleic acids according to a sixth aspect of the present invention contains nucleotides each combined at 3'- and 5'-terminals thereof with respective particles having different particle sizes and having no labels for detection.

The reagent used for measuring nucleic acids according to a seventh aspect of the present invention contains nucleotides each combined at one of 3'- and 5'-terminals thereof with a particle having a label for detection and at the other terminal with a magnetic particle.

The reagent used for measuring nucleic acids according to an eighth aspect of the present invention contains nucleotides each combined at one of 3'- and 5'-terminals thereof with a particle having no label for detection and at the other terminal with a magnetic particle.

The reagent used for measuring nucleic acids according to a ninth aspect of the present invention wherein said reagent contains nucleotides each combined at 3'- and 5'-terminals thereof with particles, these particles being combined respectively with other particles to produce particle aggregates in the matrix form.

Measuring principles and details of the first to ninth aspects of the present invention are as-follows.

In the first aspect of the present invention, nucleotides each combined at 3'- and 5'-terminals thereof, respectively, with first and second particles are used as a reagent. This reagent is reacted with a sample to form double-stranded nucleotides, and a double strand of each of the double-stranded nucleotides is cleaved. At this time, the first and second particles in the reagent having reacted with the sample are separated from each other by the cleaving, while the first and second particles in the unreacted reagent are not subjected to cleavage and kept linked together. The first and second particles subjected to the cleavage and the first and second particles not subjected to cleavage are different in size of particle masses from each other, making it possible to discriminate the particles in these two groups from each other. Therefore, by discriminating and detecting the first and second particles separated from each other by the cleaving and the first and second particles held in the unreacted reagent and not subjected to cleavage, and then counting the number of the particles in at least one group, an objective component in the sample can be measured based on the counted particle number.

Thus, it is not required in the present invention to remove the unreacted reagent from the reaction system before cleaving the formed double-stranded nucleotides. It is also not required, after cleaving the formed double-strands, to distinguish and separate the first and second particles in the reacted reagent subjected to the cleavage from the first and second particles in the unreacted reagent not subjected to cleavage.

Further, in the present invention, the labeling particles are measured not based on a concentration thereof, but by counting the number of the particles, and hence can be detected with good sensitivity.

As a result, with the present invention, an unreacted labeling reagent is no longer required to be washed and separated, enabling nucleic acids to be quickly measured with high sensitivity.

In the second aspect of the present invention, the measuring method employs a reagent containing nucleotides each combined at 3'- and 5'-terminals thereof with a binder, and first and second particles combined with said binder being capable of respectively specifically binding to the above binder. In the third aspect of the present invention, the measuring method employs a reagent containing nucleotides each combined at one of 3'- and 5'-terminals thereof with a labeling substance as a binder (binder) and at the other terminal with a first particle, and second particles each combined with a labeling substance (binder) being capable of specifically binding to said labeling substance (binder). In any of these cases, by bringing the nucleotides to contact with the first and second particles (second aspect) or the second particle (third aspect) in a solution, the labeling substances (binders) are specifically bound to each other to produce the same reagent as according to the first aspect of the present invention, i.e., a reagent containing nucleotides each combined at one of 3'- and 5'-terminals thereof respectively with the first and second particles. With either of the methods, since nucleotides and particles are combined with each other just before or during use to provide a complete reagent, a risk that the nucleotides and the particles may be separated till the use thereof due to vibration during transportation or other causes is reduced, with the result of improved reliability as a reagent.

Various processes are conceivable as methods of detecting particles. A method of allowing a solution containing particles to pass through a flow cell, irradiating light to the flow cell, and detecting responses to the irradiated light, thereby discriminating the existence of label or size for each of particle masses. Practically, a flow cytometer can be used.

As the particles used in the present invention, fluorescent or non-fluorescent fine particles, or magnetic fine particles are preferable. Latex particles or inorganic materials particles can also be used as the particles. In addition, gels such as SEPHADEX™ ion-exchange resins and the like may also be used. These various materials can each be treated to contain functional groups or no functional groups depending on whether covalent bonds or non-covalent bonds are desired. For example, the particles can be treated to contain amino groups as functional groups. This treatment is performed by attaching alkylamine, hydrazine or thiosemicarbazide to the particles. The particle size is preferably in the range of 0.01 to 10.0 μm, particularly preferably 0.01 to 1.0 μm.

In the case of using a flow cytometer, fluorescent fine particles can be preferably used. The fluorescent fine particles practically include those which have fluorescent material layers at the surfaces of non-fluorescent fine particles, or those which are obtained by granulating a mixture of a fluorescent material and a composition for granulation. The flow cytometer detects the intensity of fluorescence and counts the number of particles passing through a flow cell. The fluorescent material for the fluorescent fine particles includes fluorescein, coumarin derivatives, rhodamine derivatives, umbelliferone and the like, which are well-known.

The light emitting particles are not limited to the fluorescent particles, but may be of luminescent particles. Alternatively, they may be of another type labeling particles or particles having no labels for detection.

The objective to be measured is a single-stranded nucleotide (DNA, RNA). If a nucleotide contained in the sample has a double strand, this double strand must be changed into a single strand before start of the measurement. The sample nucleotide can be denatured to have a single strand by dipping it in an alkaline solution or by quickly cooling it after boiling.

A nucleotide used here as the reagent is that which can form a double-stranded nucleotide with a nucleotide to be measured and can be synthesized. The reagent nucleotide used in the present invention was, by way of example, an oligonucleotide of 30 bases synthesized by the phosphoamidite method using a DNA synthesizer Model 381A supplied by Applied Biosystems Corp. The size of the reagent nucleotide is usually about 15 bases or more and, in some cases, 50 bases or more. The region for hybridization between the reagent nucleotide and the sample has 16 bases or more in most of the cases. Although the homology percentage need not be 100%, it is preferably at least about 50%, more preferably at least 80%.

A process of binding a nucleotide to a particle can be performed by any of well-known methods, such as a chemically binding method and physically adsorbing method, depending on the particle used. For example, various methods described in J. A. Matthews & L. J. Kricka, "Analytical Strategies for the Use of DNA Probes", Analytical Biochemistry 169, pp1–25, 1988 can be used. That is, the usage of a solid phase is reviewed in "4.1. Solid Support" on page 14 of the article and summarized in Table 7 on page 15. Of the column "Solid Support" in Table 7, SEPHACRYL S-500, Cellulose/magnetic beads, CNBr-SEPHROSE 4B, Latex microparticles, and SEPHADEX G-50 correspond to the particles used in the present invention. Various methods of binding a solid phase and a DNA (oligonucleotide) are also described in the column "Binding to support" in Table 7.

To cleave the double-stranded nucleotide, a restriction enzyme (restriction endonuclease), or hydrolase such as phosphodiesterase, peptidase and esterase can also be used. The restriction enzyme has a function of recognizing a particular location in the base sequence and severing a double-stranded nucleotide. Accordingly, if the base sequence of a nucleotide used as the reagent contains, even at only one location thereof, the sequence recognizable by a restriction enzyme, the nucleotide can be cleaved by allowing the restriction enzyme to act thereon. In other words, so long as the above condition is satisfied, any restriction enzyme can freely be selected.

As the binder to be attached to the nucleotide and/or the particle, a binder having a property of specifically reacting therewith, such as biotin, avidin or hapten, may be used. For example, a reagent of nucleotides each combined at its 3'-terminal with biotin and at its 5'-terminal with hapten, a reagent of particles each bound to avidin specifically reacting with biotin, and a reagent of particles each bound to an antihapten antibody specifically reacting with hapten can be reacted with a sample. As an alternative example, a reagent of nucleotides each combined at its 3'-terminal with biotin and at its 5'-terminal with a particle, and a reagent of particles each bound to avidin may be reacted with a sample.

A process of attaching the binder to the nucleotide and/or the particle can be performed in accordance with the methods which are well-known. Methods of labeling a nucleotide by biotin, avidin or hapten are described in, e.g., "Labeling Procedures" of the above-cited Analytical Biochemistry 169, 1–25, 199, page 9.

The fourth to ninth aspects of the present invention are derived by further specifying the types of the particles in the first aspect of the invention.

In the fourth aspect of the present invention, nucleotides each combined at 3'- and 5'-terminals thereof with light emitting particles, e.g., fluorescent particles, are used as a reagent. This reagent is reacted with a sample to form double-stranded nucleotides, and a double strand of each of the double-stranded nucleotides is cleaved by an enzyme. The particles bound to both terminals of the nucleotide may have the same size or different sizes. Since the particles separated from each other by cleaving the double strands and the particles held in the unreacted reagent and not subjected to cleavage are different in the size of particle masses from each other, these two groups of particles can be discriminated from one another and detected. By counting the number of the particles in at least one group, nucleotides as an objective component in the sample can be measured. The method according to this aspect does not require a step of separating the particles in the reagent having reacted with the sample from the particles in the unreacted reagent, or a step of separating the particles in the reacted reagent subjected to the cleavage of the double strands from the particles in the unreacted reagent not subjected to cleavage, or a further a step of washing.

In the fifth aspect of the present invention, nucleotides each combined at one of 3'- and 5'-terminals thereof with a light emitting particle, e.g., a fluorescent particle and at the other terminal with no label for detection, are used as a reagent. This reagent is reacted with a sample to form double-stranded nucleotides, and a double strand of each of the double-stranded nucleotides is cleaved by an enzyme. The two types of particles used here are preferably different in particle size. After cleaving the double strands, the intensities of fluorescences and the intensities of scattered lights from the particles separated from each other by the cleaving and the particles held in the unreacted reagent and not subjected to cleavage, are measured simultaneously to count the number of the particles in at least one group. As a result, nucleotides as an objective component in the sample can be measured with no need of separation and washing.

In the sixth aspect of the present invention, nucleotides each combined at 3'- and 5'-terminals thereof with respective particles having different sizes and having no labels for detection are used as a reagent. This reagent is reacted with a sample to form double-stranded nucleotides, and a double strand of each of the double-stranded nucleotides is cleaved by an enzyme. After cleaving the double strands, the small- and large-size particles separated from each other by the cleaving and the particles held in the unreacted reagent and not subjected to cleavage are largely different in particle size from each other. Therefore, by measuring the intensities of scattered lights from the particles, those different groups of particles can be discriminated from one another and detected. By counting the number of the particles in at least one group, nucleotides can be measured as an objective component in the sample.

In the seventh aspect of the present invention, nucleotides each combined at one of 3'- and 5'-terminals thereof with a labeling particle, e.g., a fluorescent particle and at the other terminal with a magnetic particle, are used as a reagent. This reagent is reacted with a sample to form double-stranded nucleotides, and a double strand of each of the double-stranded nucleotides is cleaved by an enzyme. After cleaving the double strands, by attracting the magnetic particles by a magnet and measuring the fluorescent particles liberated by the cleaving, nucleotides as an objective component in the sample can be measured. With this method, it is not necessary to perform a centrifugal operation or filter sorting for separating the labeling particles in the reagent having reacted with the sample from the particles in the unreacted labeling reagent. Specifically, after cleaving the double strands, by measuring the fluorescent particles liberated by cleavage and residing in supernatant liquid under a condition in which the magnetic particles are attracted by a magnet disposed under a reaction vessel, nucleotides as an objective component in the sample can be measured with no need of particularly separating and washing the particles in the reacted reagent subjected to cleavage, and the particles in the unreacted reagent not subjected to cleavage. Instead of measuring the free fluorescent particles in supernatant liquid of the reaction solution, the fluorescent particles bound to the magnetic particles which are attracted by the magnet (i.e., the fluorescent particles in the unreacted reagent) may be measured.

In the eighth aspect of the present invention, nucleotides each combined with a particle having no label for detection are used in place of the fluorescent labeling particle used in the method according to the seventh aspect and are used as a reagent. Similar to the seventh aspect, this reagent is reacted with a sample to form double-stranded nucleotides, a double strand of each of the double-stranded nucleotides is cleft, and the magnetic particles are attracted by a magnet. Then, the particles liberated by cleavage are measured under a condition in which the magnetic particles are attracted by a magnet disposed under a reaction vessel. Measurement of the particles is carried out by detecting the intensity of scattered light. As with the seventh aspect, it is not necessary to perform a centrifugal operation or filter sorting for separating the particles in the reagent having reacted with the sample from the particles in the unreacted reagent. It is also not necessary to separate and wash the particles subjected to cleavage of the double strands and the particles not subjected to cleavage.

In the ninth aspect of the present invention, nucleotides combined at 3'- and 5'-terminals with particles, these particles being bound to other particles to produce particle aggregates in the matrix form, are used as a reagent. This reagent is reacted with a sample to form double-stranded nucleotides, and a double strand of each of the double-stranded nucleotides is cleaved by an enzyme. Upon cleavage of the double strands, the particle aggregates in the matrix form are divided to produce segments of the particle aggregates having reduced matrix size. Therefore, by measuring the particle aggregates and/or their segments, nucleotides as an objective component in the sample can be determined. The particles used here may be labeling particles such as fluorescent particles, or of particles having no labels. With this method, since the intensity of fluorescence or the intensity of scattered light from the particle aggregates in the matrix form is measured, the intensity of fluorescence or the intensity of scattered light to be detected is amplified so that the particle aggregates in the reagent having reacted with the sample and the particle aggregates in the unreacted reagent can be discriminated from one another with improved accuracy, and hence detected with higher sensitivity. This methods also requires neither a step of separating the particles in the reagent having reacted with the sample from the particles in the unreacted reagent, nor a step of separating and washing the particles subjected to cleavage of the double strands and the particles not subjected to cleavage.

In addition, when carrying out the measuring method of the present invention, it is preferable to use a reagent kit including a reagent of nucleotides specifically reacting with a component to be measured, and a reagent of particles capable of binding to those nucleotides or having been bound thereto. In this case, it is more preferable for the kit to further include an enzyme capable of cleaving the formed double strands. These reagents may be put in respective containers.

BRIEF DESCRIPTION OF THE DRAWINGS

FIG. 13 is a table showing measured results obtained by carrying out the first embodiment of the present invention by using the automatic analyzer shown in FIG. 12.

FIG. 14 is a table showing measured results obtained by carrying out the fourth embodiment of the present invention by using the automatic analyzer shown in FIG. 12.

DETAILED DESCRIPTION OF THE PREFERRED EMBODIMENTS

Embodiments of the measuring methods and the reagents used therefor according to the present invention will first be described with reference to the drawings.

First Embodiment

Figure 1:
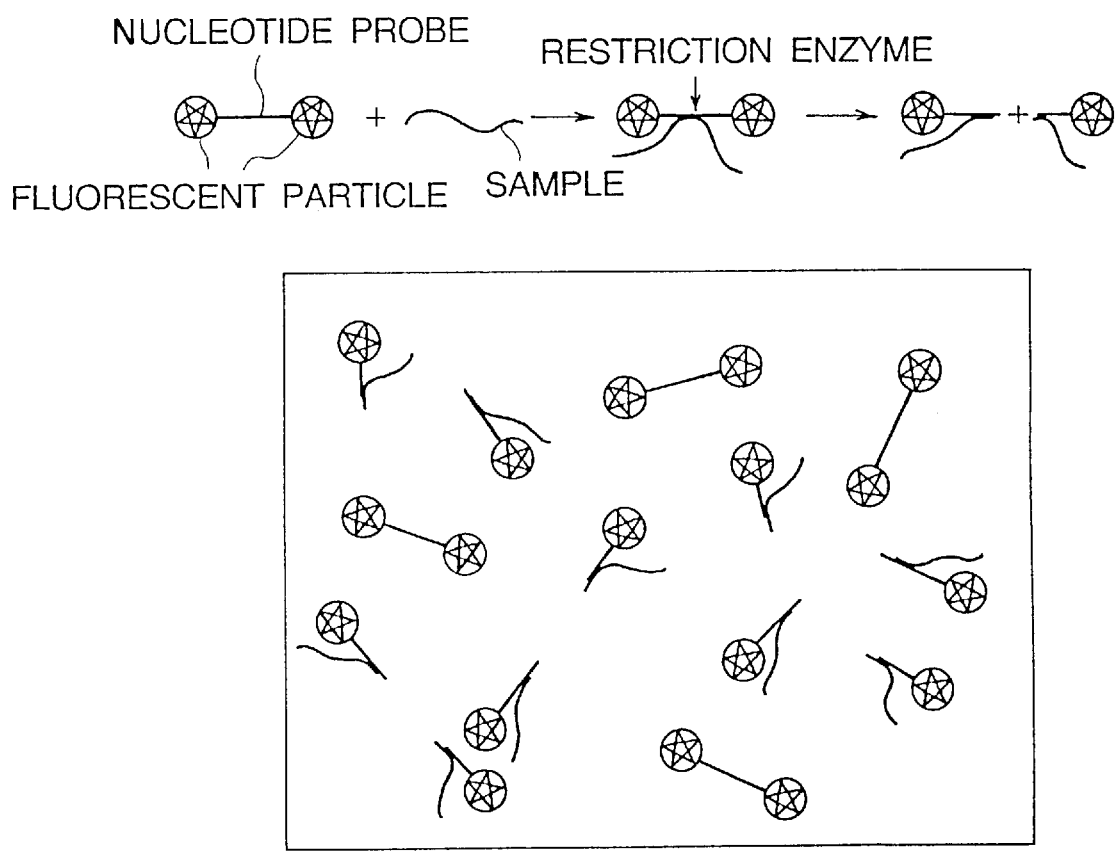
FIG. 1 is an illustration to explain measuring principles in a method of measuring nucleic acids according to a first embodiment of the present invention.

This embodiment corresponds to the above fourth aspect of the present invention. As shown in FIG. 1, a reagent containing nucleotides each combined at 3'- and 5'-terminal thereof with fluorescent particles is mixed to a sample to form double-stranded nucleotides, and an enzyme is then allowed to act on the formed double-stranded nucleotides to cleave their double strands. The fluorescent particles liberated by cleavage (i.e., free particles) emit fluorescences at the smaller intensity than emitted from the unreacted reagent in which the fluorescent particles remain bound to both the terminals of the nucleotide. By utilizing this difference, these two groups of particles can be discriminated from one another and detected. Although the fluorescent particles bound to both the terminals of the nucleotide may have the same particle size or different sizes, they are assumed to have the same size in this embodiment. When the fluorescent particles bound to both the terminals have the same particle size, the number of the free particles in the reaction solution after the cleaving by an enzyme corresponds to twice the amount of nucleotides in a sample to be measured if those fluorescent particles are bound to a single nucleotide. Therefore, by counting the free particles, the amount of nucleotides measured can be determined. In an attempt to bind fluorescent particles to both terminals of a nucleotide, however, the fluorescent particles are often bound to both terminals of plural, common nucleotides. In such a case, a calibration curve for the relationship between the number of free particles and the amount of nucleotides in a sample is prepared beforehand by measuring a plurality of reference samples, on which the amounts of nucleotides are known, in accordance with the method of the present invention. By utilizing this calibration curve, the amount of nucleotides in a sample can also be determined from the measured value of the number of free particles.

Figure 2:
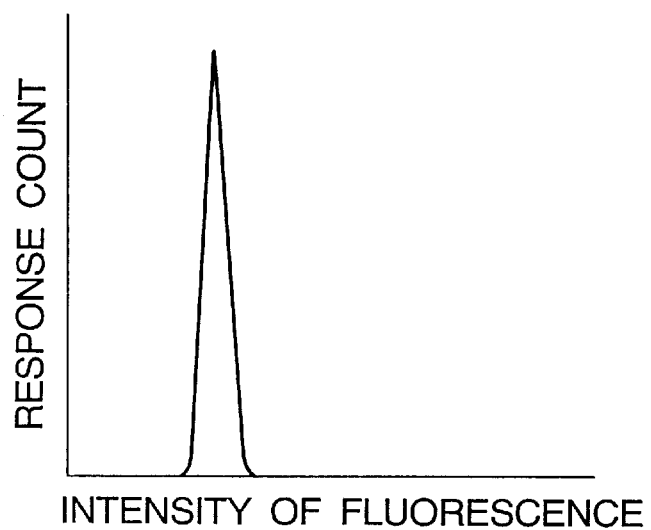
FIG. 2 is a graph showing data of the intensity of fluorescence from fluorescent particles separated by cleaving, as measured in the first embodiment.

By way of example, measurement was conducted using a commercially available flow cytometer, flowing a reaction solution to pass through a flow cell, irradiating light to the flow cell, and detecting responses to the irradiated light. The detected result is shown in FIG. 2. The response count represented by the vertical axis coincides with the number of the fluorescent particles separated or liberated by cleavage (i.e., free particles), and a known certain proportion of the number of those fluorescent particles coincides with the number of the reacted nucleotides. Therefore, the number of nucleotides of interest in a sample can be measured from the response count. Alternatively, as the amount of the nucleotide reagent used is known (or fixed), the amount of nucleotides to be measured can also be determined by counting the number of the particles in the unreacted reagent after cleavage with an enzyme.

The intensities of fluorescences from the free particles contained in the reagent of nucleotides each combined at both terminals thereof with fluorescent particles (i.e., the reagent blank solution) and the particles in the unreacted reagent are measured to determine reagent blank values. No free particles are present by nature in the reagent blank solution, and all the particles therein are those held in the unreacted reagent. However, there is a possibility that free particles may be mixed in the reagent blank solution during the stage of preparation or storage of the reagent. Since the reagent blank value corresponds to a background level of the reaction, the number of the free particles which has been compensated for the reagent blank can be determined by subtracting the measured value of the free particles in the sample reaction solution from the measured value of the free particles in the reagent blank solution.

When determining the amount of nucleotides in a sample to be measured, the amount of nucleotides may be determined by counting only the free particles, but accuracy of the measurement can be improved by counting the particles in the unreacted reagent. More specifically, in the case where fluorescent particles are bound to both terminals of a single nucleotide, by way of example, it is expected that the number of free particles which has increased from the reagent blank value is equal to a value twice the number of the particles in the unreacted reagent which has decreased from the reagent blank value, but both the values may not coincide with each other, such as trouble during detection of the particles. Therefore, the number of the particles in the unreacted reagent is also counted and a value twice the number by which the number of the particles in the unreacted reagent which has decreased from the reagent blank value is compared with a value by which the number of the free particles has increased from the reagent blank value. If the difference between both the values is large, then another measurement is required. As a result, higher-accurate data can be obtained.

Instead of counting the absolute value of the free particles, the amount of nucleotides in a sample can also be determined based on the ratio of the number of the free particles to the number of the particles in the unreacted reagent. Specifically, a calibration curve for the relationship between the ratio of the number of the free particles to the number of the particles in the unreacted reagent and the amount of nucleotides in a sample is prepared beforehand by measuring a plurality of reference samples, on which the amounts of nucleotides are known, in accordance with the method of the present invention. Utilizing this calibration curve, the amount of nucleotides in a sample can be determined from the ratio of both the particle numbers. This method is advantageous in that the amount of nucleotides in a sample can be measured without counting the particles throughout the reaction solution.

As described above, the amount of nucleotides in a sample to be measured can be determined by discriminating and detecting the free particles in the reaction solution after the reaction of an enzyme cleaving a double strand and the particles in the unreacted reagent, and then counting the number of the particles in at least one group.

Second Embodiment

Figure 3:
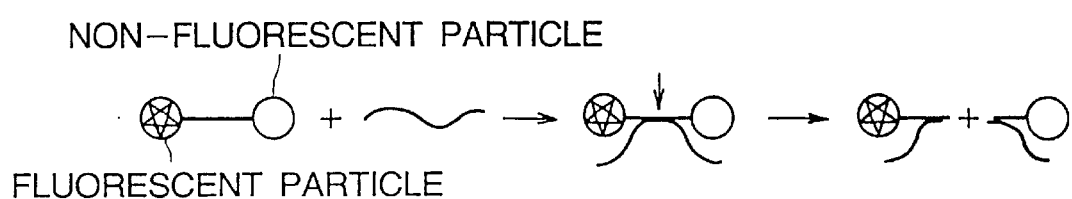
FIG. 3 is an illustration to explain measuring principles in a method of measuring nucleic acids according to a second embodiment of the present invention.
Figure 3:
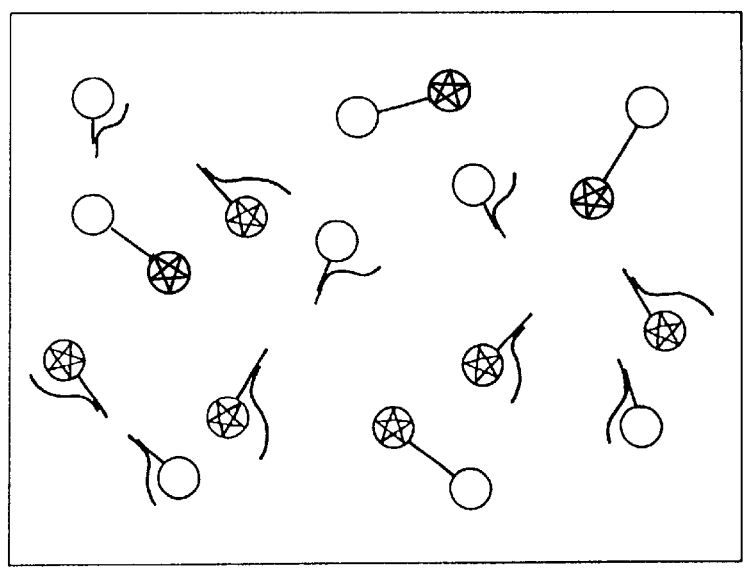

This embodiment corresponds to the above fifth aspect of the present invention. As shown in FIG. 3, a reagent containing nucleotides each combined at one of 3'- and 5'-terminals thereof with a fluorescent particle and at the other terminal with a particle having no label for detection is mixed to a sample to form double-stranded nucleotides, and an enzyme is then allowed to act on the formed double-stranded nucleotides to cleave their double strands. The particles liberated by cleavage (i.e., free particles) produce scattered lights at a smaller intensity than detected for the unreacted reagent in which the particles are kept bound to both the terminals of the nucleotide. Utilizing this difference, these two groups of particles can be discriminated from one another and detected. When the amount of nucleotides in a sample is measured based on the intensity of scattered light, a background error may come into the measured result. To compensate for such an error, the intensity of fluorescence is simultaneously measured so that the amount of nucleotides in a sample is also measured based on the intensity of fluorescence. Although the particles bound to both the terminals of the nucleotide may have the same particle size or different sizes, they are assumed to have the same size in this embodiment.

If one fluorescent particle is bound to a single nucleotide, the number of the free fluorescent particles in the reaction solution after cleavage with an enzyme coincides with the amount of nucleotides in a sample to be measured. Therefore, by counting the free fluorescent particles, the amount of nucleotides to be measured can be determined. In attempting to bind a fluorescent to one terminal of a nucleotide, however, the fluorescent particle is often bound to one terminal of plural common nucleotides. In such a case, a calibration curve for the relationship between the number of the free fluorescent particles to the amount of nucleotides in a sample is prepared beforehand by measuring a plurality of reference samples, on which the amounts of nucleotides are known, in accordance with the method of the present invention. Utilizing this calibration curve, the amount of nucleotides in a sample can also be determined from the measured value of the number of the free fluorescent particles.

Figure 4:
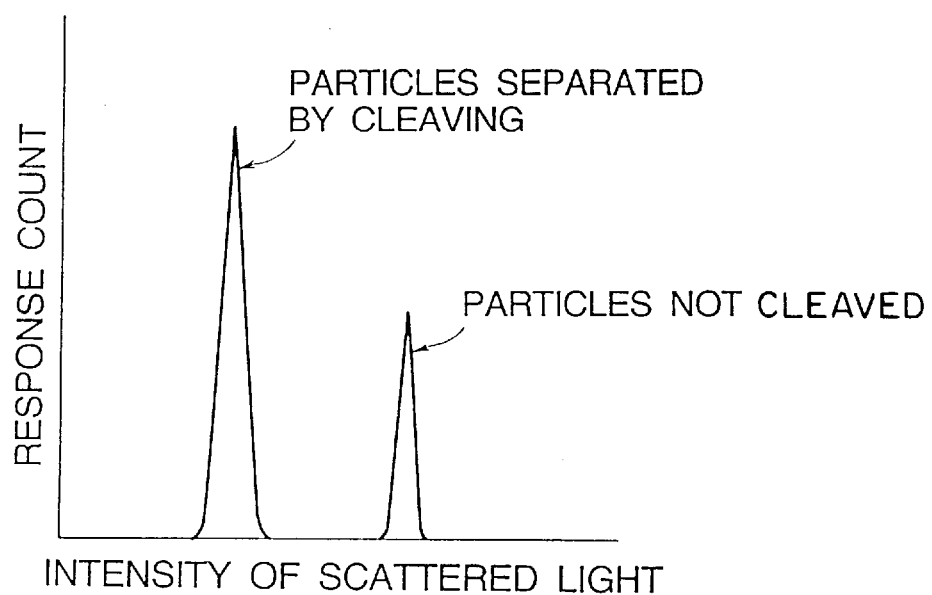
FIG. 4 is a graph showing data of the intensities of scattered lights from particles, as measured in the second embodiment.
Figure 5:
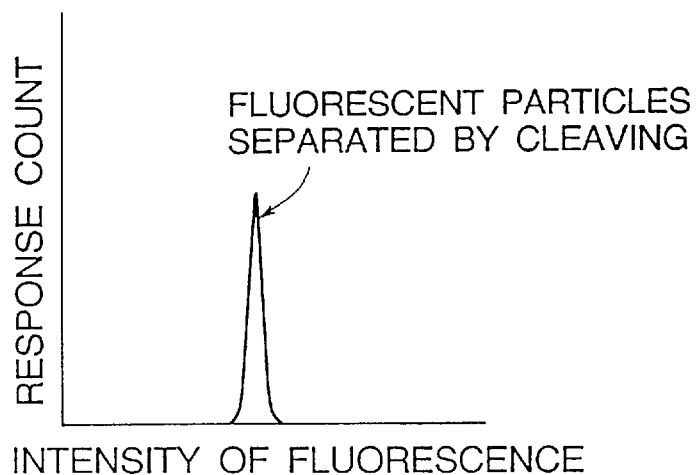
FIG. 5 is a graph showing data of the intensity of fluorescence from fluorescent particles separated by cleaving, as measured in the second embodiment.
Figure 6:
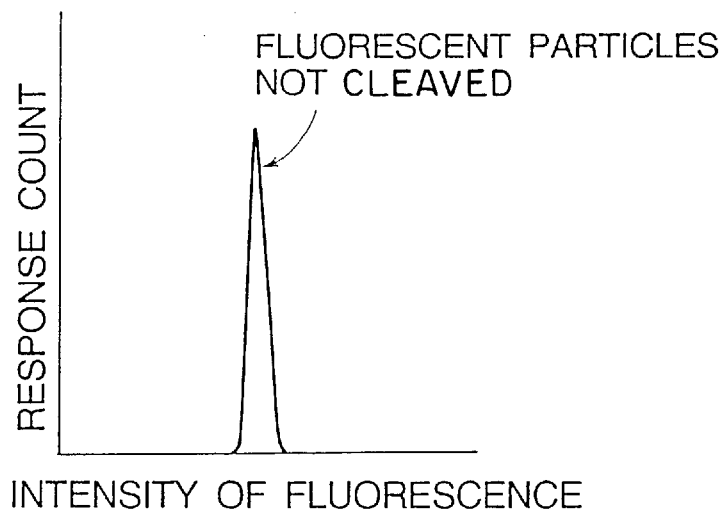
FIG. 6 is a graph showing data of the intensity of fluorescence from fluorescent particles held in the unreacted reagent and not cleaved, as measured in the second embodiment.

By way of example, measurement was conducted using a commercially available flow cytometer, flowing a reaction solution to pass through a flow cell, irradiating light to the flow cell, and detecting the intensity of fluorescence and the intensity of scattered light simultaneously. The detected results are shown in FIGS. 4 to 6. FIG. 4 shows the response count for the intensity of scattered light. As seen, the particles separated or liberated by cleavage exhibit a larger intensity of scattered light than the particles (particle masses) held in the unreacted reagent and being not cleft, resulting in two peaks. The response count represented by the peak at the smaller intensity of scattered light coincides with the number of the particles separated by cleavage, and a certain proportion of that number coincides with the number of reacted nucleotides. Therefore, the number of nucleotides in a sample can be measured from only the data of FIG. 4. But when the measurement is conducted based on the intensity of scattered light, a background error may come into the measured result. To compensate for such an error, the intensity of fluorescence is measured at the same time as measuring the intensity of scattered light so that the amount of nucleotides in a sample is also measured based on the intensity of fluorescence.

FIGS. 5 and 6 show measured data of the intensity of fluorescence. FIG. 5 indicates the response count of the fluorescent particles separated by cleavage, corresponds to the response peak at the smaller intensity of scattered light in FIG. 4, and FIG. 6 and indicates the response count of the fluorescent particles held in the unreacted reagent and not subjected to cleavage, as resulted corresponding to the response peak at the smaller intensity of scattered light in FIG. 4. The number of the fluorescent particles separated by cleavage can be determined from the data of FIG. 5, and the number of nucleotides of interest can precisely be measured from the determined number of the fluorescent particles similar to the first embodiment.

Alternatively, as the amount of the nucleotide reagent used is known, the amount of nucleotides to be measured can also be determined from the data of FIG. 6 obtained by counting the number of the fluorescent particles in the unreacted reagent after cleavage with an enzyme.

Further, this embodiment is similar to the first embodiment in that the intensities of fluorescences from the free particles contained in the reagent blank solution and the particles in the unreacted reagent are measured to determine reagent blank values, to obtain the amount of nucleotides in a sample which has been compensated for the reagent blank. Accuracy of the measurement is improved by simultaneously counting the free particles and the particles in the unreacted reagent, and the amount of nucleotides in a sample can also be determined based on the ratio of the number of the free particles to the number of the particles in the unreacted reagent instead of counting the absolute value of the free particles.

As described above, the amount of nucleotides in a sample to be measured can be determined by simultaneously discriminating and detecting the free particles in the reaction solution after the reaction of an enzyme cleaving a double strand and the particles in the unreacted reagent, and then counting the number of the particles in at least one group.

Third Embodiment

Figure 7:
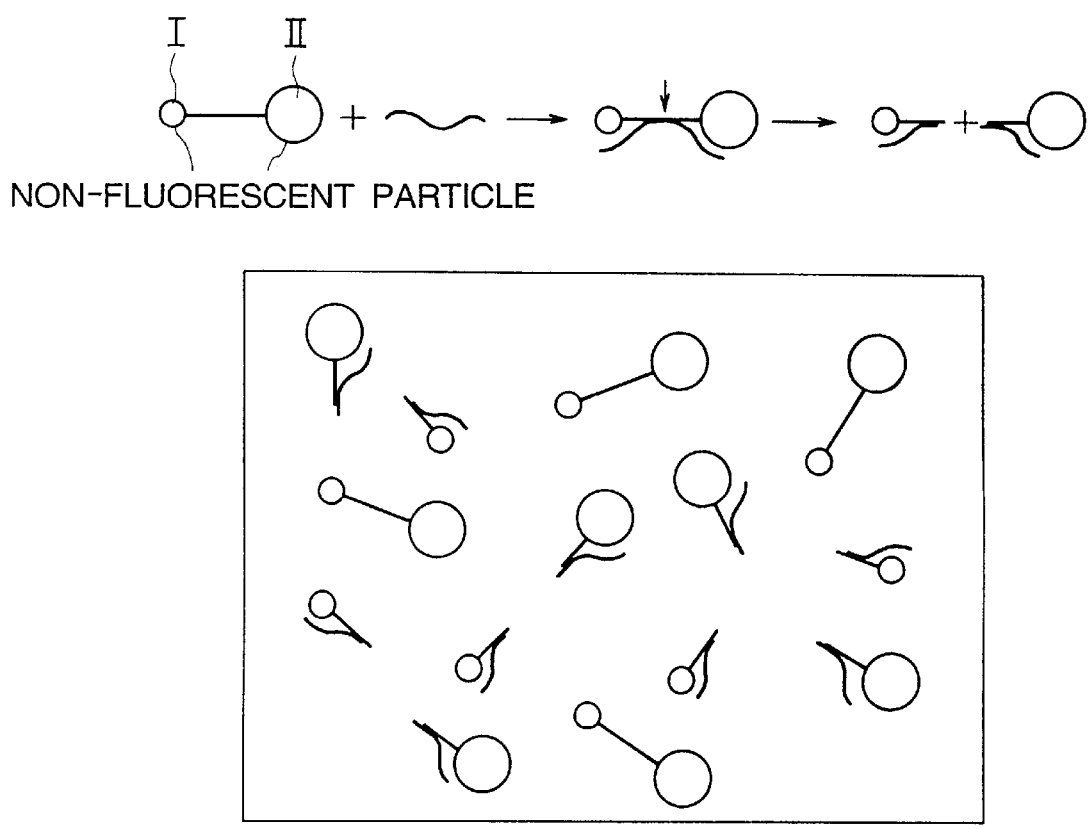
FIG. 7 is an illustration to explain measuring principles in a method of measuring nucleic acids according to a third embodiment of the present invention.

This embodiment corresponds to the above sixth aspect of the present invention. As shown in FIG. 7, a reagent containing nucleotides each combined at 3'- and 5'-terminals thereof respectively with a particle I and a particle II having different particle sizes and having no labels for detection is mixed to a sample to form double-stranded nucleotides, and an enzyme is then allowed to act on the formed double-stranded nucleotides to cleave their double strands. The small-size particles liberated by cleavage (i.e., free particles I) are largely different in particle size from the large-size particles (free particles II) and the unreacted reagent in which the particles are bound to both terminals of the nucleotide, and hence produce scattered lights at the smaller intensity. Utilizing this difference, these two groups of particles can be discriminated from one another and detected. The easier the discrimination, the larger is the difference in particle size between the particles I and the particles II.

If the particle I and the particle II are bound to a single nucleotide, the number of the free particles I in the reaction solution after cleavage with an enzyme coincides with the amount of nucleotides in a sample to be measured. Therefore, by counting the free particles I, the amount of nucleotides to be measured can be determined. In attempting to bind the particles I and II to both terminals of a single nucleotide, however, particles I and II are often bound to both terminals of plural common nucleotides. In such a case, a calibration curve for the relationship between the number of free particles I to the amount of nucleotides in a sample is prepared be forehand by measuring a plurality of reference samples, on which the amounts of nucleotides are known, in accordance with the method of the present invention. By utilizing this calibration curve, the amount of nucleotides in a sample can also be determined from the measured value of the number of the free particles I.

Figure 8:
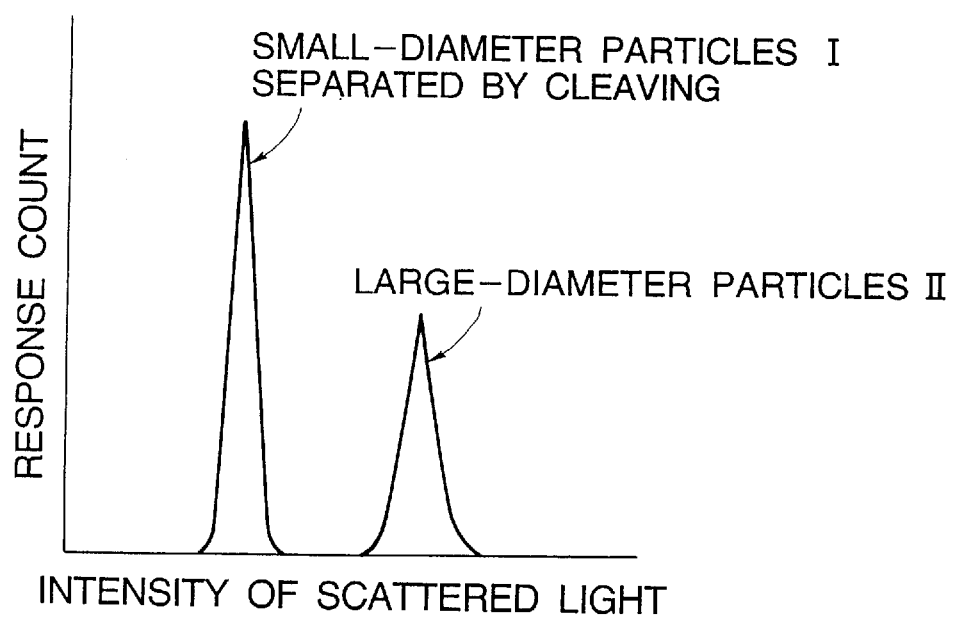
FIG. 8 is a graph showing data of the intensities of scattered lights from particles, as measured in the third embodiment.

By way of example, measurement was conducted using a commercially available flow cytometer, flowing a reaction solution to pass through a flow cell, irradiating light to the flow cell, and detecting the intensity of fluorescence and the intensity of scattered light simultaneously. The detected result is shown in FIG. 8. The response count represented by the peak at the smaller intensity of scattered light coincides with the number of small-size particles I separated by cleavage, and the response count represented by the peak at the larger intensity of scattered light coincides with the number of large-size particles II. A certain proportion of the number of small-size particles I coincides with the number of reacted nucleotides and, therefore, the number of nucleotides of interest can be measured from the response count.

Alternatively, as the number of all the particles II as a total of the free particles II and the particles II in the unreacted reagent coincides with the amount of the nucleotide reagent used, the amount of nucleotides measured can also be determined by counting the total number of the particles II after cleavage with an enzyme, i.e., from the response count of the large-size particles II in FIG. 8, if the amount of the nucleotide reagent used is known.

Further, this embodiment is similar to the first embodiment in that the intensities of scattered lights from the free particles I and all the particles II contained in the reagent blank solution are measured to determine reagent blank values, to obtain the amount of nucleotides in a sample which has been compensated for the reagent blank. Accuracy of the measurement is improved by simultaneously counting the free particles I and all the particles II, and the amount of nucleotides in a sample can also be determined based on the ratio of the number of the free particles I to the number of all the particles II, instead of counting the absolute value of the free particles I.

As described above, the amount of nucleotides in a sample to be measured can be determined by discriminating and detecting the small-size free particles I and the large-size free particles II in the reaction solution after the reaction with an enzyme which cleaves a double strand and the particles in the unreacted reagent, and then counting the number of the particles in at least one group.

Fourth Embodiment

Figure 9:
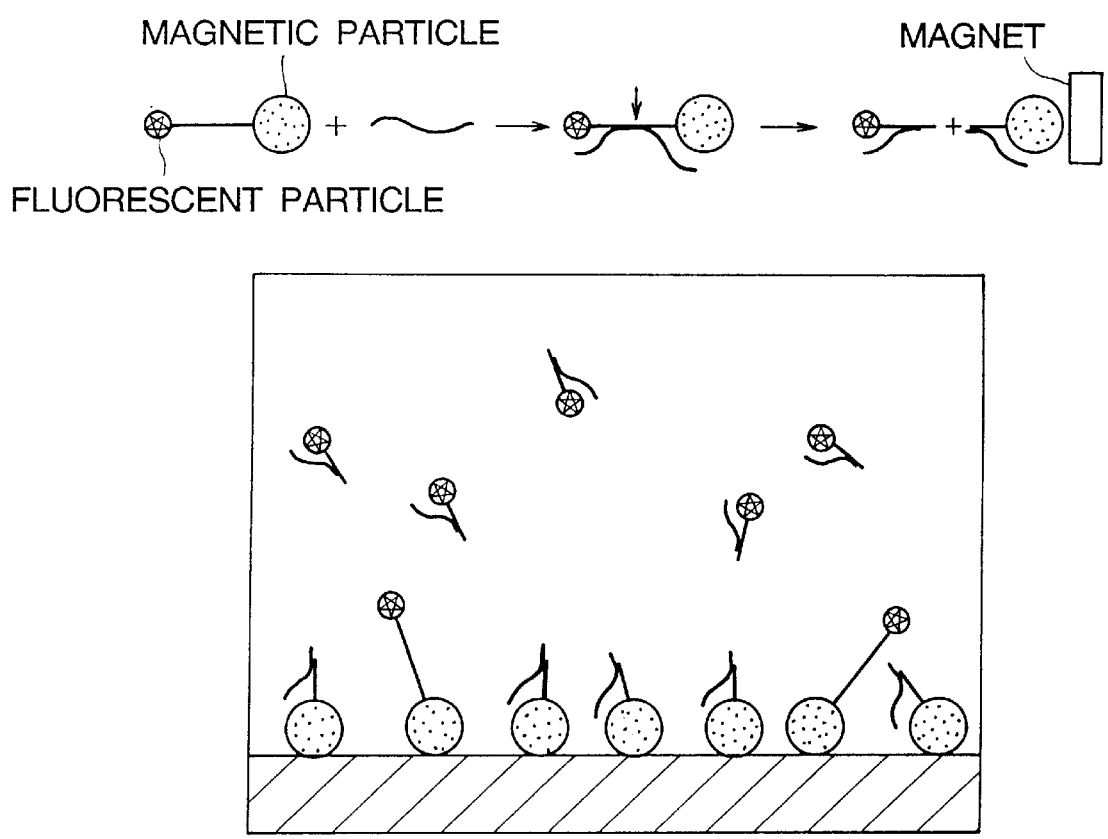
FIG. 9 is an illustration to explain measuring principles in a method of measuring nucleic acids according to a fourth embodiment of the present invention.

This embodiment corresponds to the above seventh aspect of the present invention. As shown in FIG. 9, a reagent containing nucleotides each combined at one of 3'- and 5'-terminals thereof with a fluorescent particle and at the other terminal with a magnetic particle is mixed to a sample to form double-stranded nucleotides, and an enzyme is then allowed to act on the formed double-stranded nucleotides to cleave their double strands. After cleaving the double strands, liberated magnetic particles are attracted by a magnet, while liberated fluorescent particles in the reaction solution (i.e., free particles) are discriminated from one another and detected.

If a fluorescent particle and a magnetic particle are bound to both terminals of a single nucleotide, the number of the fluorescent particles liberated in the reaction solution after cleavage with an enzyme coincides with the amount of nucleotides in a sample to be measured. Therefore, by counting the free fluorescent particles, the amount of nucleotides to be measured can be determined. In attempting to bind particles to both terminals of a nucleotide, however, the particles are often bound to both terminals of plural, common nucleotides. In such a case, a calibration curve for the relationship between the number of the free fluorescent particles to the amount of nucleotides in a sample is prepared beforehand by measuring a plurality of reference samples, on which the amounts of nucleotides are known, in accordance with the method of the present invention. Utilizing this calibration curve, the amount of nucleotides in a sample can also be determined from the measured value of the number of the free fluorescent particles.

By way of example, measurement was conducted by using a commercially available flow cytometer, flowing supernatant liquid of a reaction solution to pass through a flow cell, irradiating light to the flow cell, and detecting the intensity of fluorescence. The result is similar to the data of the first embodiment shown in FIG. 2 and, therefore, the number of nucleotides of interest can be measured from the response count.

Alternatively, by removing the supernatant liquid, which contains the free particles, from the reaction solution and then releasing the magnetic field, the fluorescent particles in the unreacted reagent can also be measured. As the amount of the nucleotide reagent used is known, the amount of nucleotides to be measured can also be determined by counting the fluorescent particles in the unreacted reagent.

Further, this embodiment is similar to the first embodiment in that the intensities of fluorescences from the free particles contained in the reagent blank solution and the particles in the unreacted solution are measured to determine reagent blank values, to obtain the amount of nucleotides in a sample which has been compensated for the reagent blank. Accuracy of the measurement is improved by simultaneously counting the free particles and the particles in the unreacted solution, and the amount of nucleotides in a sample can also be determined based on the ratio of the number of the free particles to the number of the particles in the unreacted solution instead of counting the absolute value of the free particles.

As described above, the amount of nucleotides in a sample to be measured can be determined by discriminating and detecting the free particles in the reaction solution after reaction with an enzyme which cleaves a double strand and the particles in the unreacted reagent, and then counting the number of the particles in at least one group.

Fifth Embodiment

Figure 10:
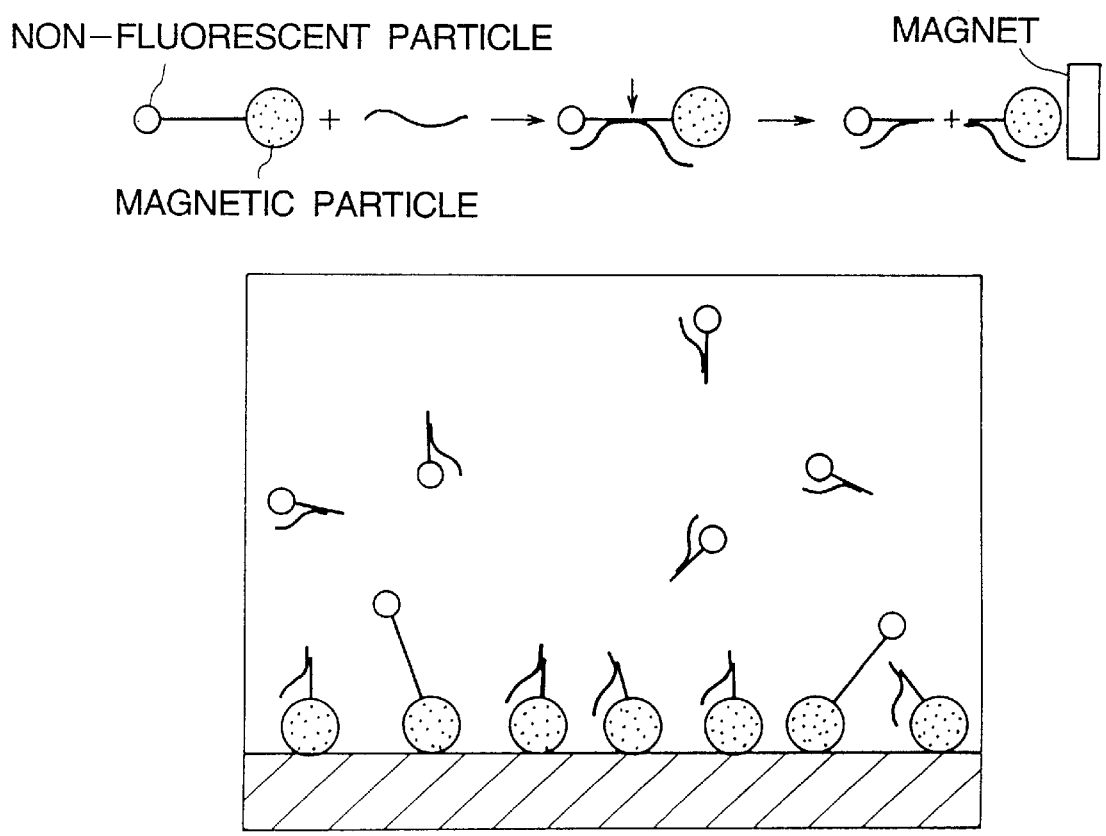
FIG. 10 is an illustration to explain measuring principles in a method of measuring nucleic acids according to a fifth embodiment of the present invention.

This embodiment corresponds to the above eighth aspect of the present invention. As shown in FIG. 10, a reagent containing nucleotides each combined at one of 3'- and 5'-terminals thereof with a particle having no label for detection, and at the other terminal with a magnetic particle is mixed to a sample to form double-stranded nucleotides. An enzyme is then allowed to act on the formed double-stranded nucleotides to cleave their double strands. After cleaving the double strands, liberated magnetic particles are attracted by a magnet, while liberated fluorescent particles in the reaction solution (i.e., free particles) are detected to count the number of the free particle based on the intensity of scattered light therefrom. Thus, the amount of nucleotides to be measured can be determined in accordance with the similar principles to those of the fourth embodiment. Also, the amount of nucleotides to be measured can be determined in accordance with the similar principles to those of the third embodiment by removing supernatant liquid, which contains the free particles, from the reaction solution, releasing the magnetic field, and then counting the number of the particles in the unreacted reagent.

With this embodiment, therefore, the amount of nucleotides in a sample to be measured can also be determined by discriminating and detecting the free particles in the reaction solution after the reaction of an enzyme cleaving a double strand and the particles in the unreacted reagent, and then counting the number of the particles in at least one group.

Sixth Embodiment

Figure 11:
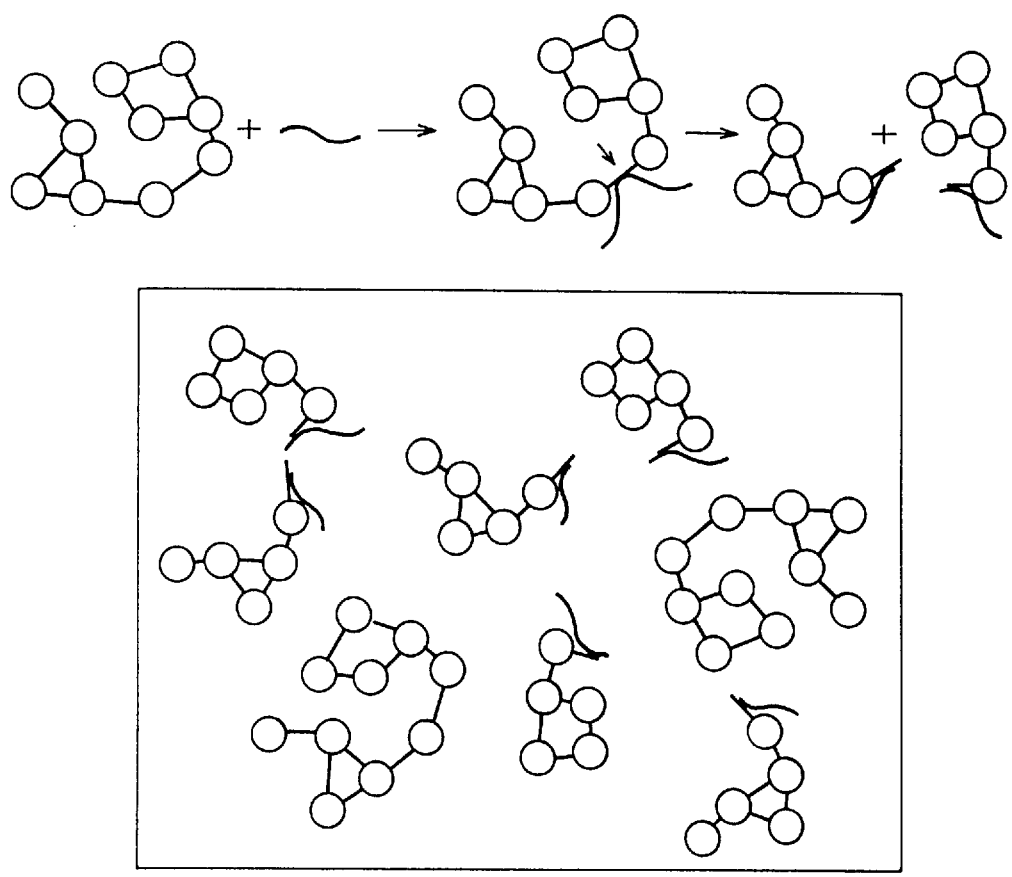
FIG. 11 is an illustration to explain measuring principles in a method of measuring nucleic acids according to a sixth embodiment of the present invention.

This embodiment corresponds to the above ninth aspect of the present invention. As shown in FIG. 11, a reagent containing nucleotides each combined at 3'- and 5'-terminals thereof with particles having no labels, these particles being bound to other particles to produce particle aggregates in the matrix form, is mixed with a sample to form double-stranded nucleotides. An enzyme is then allowed to act on the formed double-stranded nucleotides to cleave their double strands. The particle aggregates in matrix form produce a larger intensity than produced by a single particle. Also, the intensity of scattered light detected for the particle aggregates liberated by the cleaving (i.e., free particle aggregates) is much smaller than detected for the particle aggregates in the unreacted reagent. Utilizing this difference, these two groups of particles can be discriminated from one another and detected.

If the particle aggregates in matrix form are bound to both terminals of a single nucleotide, the number of the free particle aggregates in the reaction solution after cleaving with an enzyme coincides with a value twice the amount of nucleotides in a sample to be measured. Therefore, by counting the free particle aggregates, the amount of nucleotides to be measured can be determined. In attempting to bind particle aggregates in the matrix form to both terminals of a nucleotide, however, the particle aggregates are often bound to both terminals of plural, common nucleotides. Further, depending on the amount of nucleotides in a sample, the particle aggregates may be divided into a plurality of free particle aggregates as a result of the enzyme reaction. In such a case, a calibration curve for the relationship between the number of the free particle aggregates to the amount of nucleotides in a sample is prepared beforehand by measuring a plurality of reference samples, on which the amounts of nucleotides are known, in accordance with the method of the present invention. Utilizing this calibration curve, the amount of nucleotides in a sample can also be determined from the measured value of the number of the free particle aggregates.

Alternatively, as the amount of the nucleotide reagent used is known, the amount of nucleotides to be measured can also be determined by counting the number of the free particle aggregates in the unreacted reagent after cleavage with an enzyme.

Further, this embodiment is similar to the first embodiment in that the intensities of scattered lights from the free particle aggregates contained in the reagent blank solution and the particle aggregates in the unreacted reagent are measured to determine reagent blank values, thereby obtaining the amount of nucleotides in a sample which has been compensated for the reagent blank. Accuracy of the measurement is improved by simultaneously counting the free particle aggregates and the particle aggregates in the unreacted reagent, and the amount of nucleotides in a sample can also be determined based on the ratio of the number of the free particle aggregates to the number of the particle aggregates instead of counting the absolute value of the free particle aggregates.

Additionally, the particles used in this embodiment may be labeling particles such as fluorescent particles. When fluorescent particles, for example, are used to form the particle aggregates in the matrix form, sensitivity of the measurement can be further improved.

As described above, the amount of nucleotides in a sample to be measured can be determined by discriminating and detecting the free particle aggregates and in the reaction solution after the reaction with an enzyme cleaving a double strand and the particle aggregates in the unreacted reagent, and then counting the number of the particle aggregates in at least one group.

An automatic analyzer used for carrying out the measuring method of the present invention will be described below.

Figure 12:
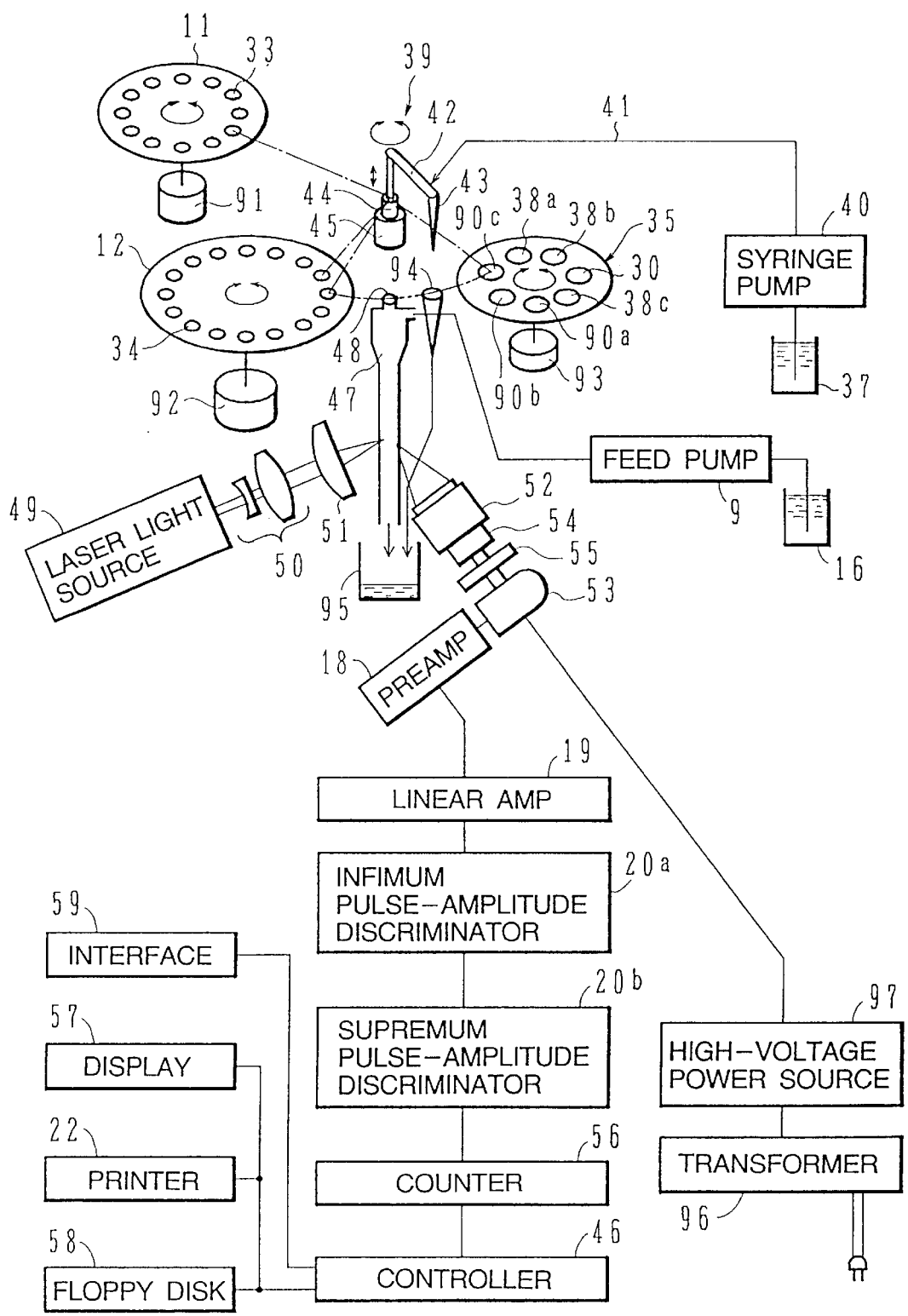
FIG. 12 is a schematic view of an automatic analyzer used for carrying out the measuring method of the present invention.

Referring to FIG. 12, the automatic analyzer suited for use with any of the above-described embodiments includes three turntables 11, 12 and 35. On the turntable 11, a plurality of sample containers 33 containing the test samples such as blood are disposed in a circle. On the turntable 12, a plurality of reaction vessels 34 are arranged in a circle. The turntables 11, 12 are designed to be turned respectively by pulse motors 91, 92, operation of each of which is controlled by a controller 46 so that a desired sample container 31 or reaction vessel 34 will be stopped at the position of suction by a pipetting nozzle 43. Transfer of the sample in each sample container 33 is accomplished by the pipetting nozzle 43. A fixed amount of a sample is sucked up by the pipetting nozzle 43 and is charged into the reaction vessel 34 which has been brought to the sample charging position.

Set on the turntable 35 are a plurality of reagent containers 30 containing various reagents assigned for the specific analytical operations. That is, containers 90a, 90b, 90c of polynucleotide reagents each combined at 3'- and 5'-terminals with the same fluorescent particles, which are first reagents respectively used for the analytical items A, B, C with nucleic acid as the object of determination, and containers 38a, 38b, 38c of restriction enzyme solutions, as second reagents, corresponding to the analytical items A, B, C are held on the turntable 35. The turntable 35 is designed to be turned by a pulse motor 93, whose operation is controlled by the controller 46 to turn the turntable 35 through a desired angular distance so that a designated reagent container will be stopped at the position of suction by the nozzle 43 at proper timing. In this way, the first reagent can be pipetted into a desired reaction vessel 34 at the position of pipetting of the first reagent by the nozzle 43. Similarly, the second reagent can be pipetted into a desired reaction vessel 34 at the position of pipetting of the second reagent by the nozzle 43.

An automatic pipetting mechanism 39 comprises the aforementioned pipetting nozzle 43 secured to a movable arm 42, a driving unit 45 for turning the arm horizontally, a driving unit 44 for moving the arm 42 vertically, a syringe pump 40 connected to the nozzle 43 through a tube 41, and a tank 37 of a washing fluid which is also used as an extruding fluid. The pipetting nozzle 43 is turned in accordance with movement of the arm 42 through an arc connecting the sample sucking position on the turntable 11, the reagent pipetting position on the turntable 12, an inlet 48 of the injection chamber of a sheath flow cell 47 and a nozzle cleaning tank 94, and is capable of ascending or descending at each of those positions.

At the restriction enzyme solution pipetting position, the restriction enzyme solution is pipetted by the nozzle 43 from the restriction enzyme solution container 38 into the hybridization reaction solution of the sample and the first polynucleotide reagent combined with the fluorescent particles, which were reacted in one reaction vessel 34. After the elapse of a predetermined period of time, a suction device is operated at the sample solution collecting position, whereby the sample solution (the solution to be analyzed) is collected and guided into the sheath flow cell 47 by the nozzle 43.

The internal structure of the sheath flow cell 47 is the same as employed in the known flow cytometer, but an injecting chamber similar to that disclosed in JP, A, 2-80937 opens at the top of the cell. This allows the nozzle 43 to enter into the inlet 48 of the injection chamber to dispense the sample solution into the sheath flow cell 47. The sheath solution in a sheath solution tank 6 is pumped up and supplied into the flow cell 47 at a fixed flow rate by a feed pump 9, the supplied solution flowing down along the inner wall of the flow cell and being discharged into a waste liquid reservoir 95. The sample solution guided into the flow cell flows in the middle of the flow of the sheath solution.

A laser light source 49 is capable of emitting argon laser beam flux with an oscillation wavelength of 488 nm. This laser beam flux is widened by a beam expander 50 and then converged by a lens 51 so that it will be irradiated to the sheath flow cell 48 to focus on the flow of the sample solution therein. An objective lens 52 is used for convergence of the fluorescent light from the flow cell 47. A space filter 54 and a wavelength selecting filter 55 are provided in front of a photomultiplier 53 which functions as a photoelectric detector, thereby to eliminate the scattered light and Raman light. The output of the photo multiplier 53 is first amplified by a preamplifier 18 and then further amplified by a linear amplifier 19, and the noise is removed by an infimum pulse-amplitude discriminator 20a and a supremum pulse-amplitude discriminator 20b. Thereafter, the pulse between the two threshold values is integrated by a counter 56.

A high voltage is applied to the photomultiplier 53 through a transformer 96 and a high-voltage power source 97. The sample numbers, results of counting, calibration curves, histogram of fluorescent measurements, etc. are output by a display 57, a printer 22 and a floppy disk 58. Communication with a personal computer through an interface 59 is also possible.

In operation, when the turntable 12 is turned and a reaction vessel 34 holding a sample comes to the first reagent pipetting position, a fixed amount of the first reagent is sucked by the nozzle 43 and pipetted into the reaction vessel 34 carried to the pipetting position. Upon completion of this sequence of operations, the turntable 12 now turns counterclockwise through 360° plus one pitch of reaction vessel (one cycle) and comes to a stop. If the time in which the turntable keeps turning and stays still in one stroke is 20 seconds, the above sequence of operations is repeated with the cycle time of 20 seconds. Thus, in the case of a specific reaction vessel 34 into which the first reagent has been pipetted, its position in a state where the turntable stays still advances counterclockwise by one pitch of reaction vessel upon completion of each above cycle of the operations. For that specific reaction vessel into which the first reagent has been pipetted, the second reagent is pipetted at a position in a state where the turntable 12 stays still, for example, at a position where the reaction vessel has advanced by one pitch. At this stage, the sample and the first and second reagents have been pipetted into the reaction vessel 34, and consequently the reaction proceeds. This reaction is recorded for a given period of time until discharge of the solution by a discharging device and cleaning by a cleaning device with the cycle time of 20 seconds.

A description will now be given on the method of measuring nucleic acids according to the first embodiment of the present invention, which is carried out by using the automatic analyzer described above.

Since the reaction processes for the respective items of determination in the analysis of nucleic acids are similar to each other, here is described a process of analytical operations by taking up the case of HBV (B type hepatitis virus). The analytical items are specified depending on the type of the particle probe added after start of the operation.

In the fluorescent particle labeled polynucleotide solution container 90a, there is prepared beforehand a fluorescent labeling latex particle reagent having single-stranded HBV-DNA probe type 1 combined at both terminals thereof with fluorescent latex particles (0.1 μm in diameter) containing a coumarin derivative serving as a fluorescent substance. The single-stranded HBV-DNA probe type 1 used here has a complementary nucleotide sequence to the nucleic acid component (HBV) to be analyzed.

As for the restriction enzyme solution, there is prepared beforehand, for example, Hae III as the restriction enzyme which cleaves double-stranded DNA formed by hybridizing the single-stranded HBV-DNA probe type 1 combined with the fluorescent labeling latex particles and the sample.

Upon start of the analyzing operation, the fluorescent labeling latex particle reagent is collected from the container 90a by the nozzle 43, and is then dispensed into the reaction chamber in the corresponding reaction vessel 34, specifying this reaction vessel as the one for HBV analysis.

Into the thus prepared reaction chamber of the reaction vessel 34 is pipetted the sample collected from the sample container 33 by the nozzle 43. HBV-DNA in the sample reacts with the single-stranded HBV-DNA probe type 1 combined at both terminals with the fluorescent particles. The reaction vessel 34 is designed to maintain the reaction on the turntable 12 at a predetermined temperature (37° C.) for a predetermined period of time (15 minutes). During this period, the reaction between HBV-DNA in the sample and the single-stranded HBV-DNA probe type 1 proceeds. Then, with turn of the turntable 35, the restriction enzyme solution container 38 is brought to the suction position and a fixed amount of the solution containing the restriction enzyme Hae III 25 in the container 38 is sucked up by the pipetting nozzle 43 and pipetted into the corresponding reaction vessel 34 on the turntable 12. At this time, the fluorescent labeling latex particles are liberated. The suction device is operated at the sample solution collecting position, whereby the sample solution containing the free particles thus liberated are sucked by the pipetting nozzle 43 and guided to the sheath flow cell 47 so that the number of the free particles is counted to thereby determine an amount of nucleic acids in the sample. The polynucleotide used here was that synthesized.

FIG. 13 shows results of measuring five samples in the form of a table. Of the five samples shown in the table, the sample numbers 1 to 3 represent those taken from hepatitis patients and the sample numbers 4 and 5 represent those taken from healthy persons.

The methods of measuring nucleic acids according to the second, third and sixth embodiments of the present invention can also be carried out by using the above-described automatic analyzer similarly to the measuring method according to the first embodiment.

The measuring method according to the fourth embodiment of the present invention, in which a nucleotide combined at one of 3'- and 5'-terminals with a fluorescent labeling particle and at the other terminal with a magnetic particle employed as a particle reagent, can satisfactorily be carried out by partly improving the above-described analyzer.

Specifically, in FIG. 12, magnets are disposed in a particular region including the position of collecting the sample solution from one of the reaction vessels 34 arranged on the turntable 12 and are located around and/or under the reaction vessel 34 in that position, so that the magnetic particles cleft as a result of the reaction and the unreacted particle reagent can be trapped by the magnets. The reagent containers 90a, 90b, 90c contain particle labeled probe reagents each combined at one of 3'- and 5'-terminals with a fluorescent labeling particle and at the other terminal with a magnetic particle respectively corresponding to the analytical items A, B, C. Described below is a process of analytical operations with the method of measuring nucleic acids according to the fourth embodiment of the present invention, by taking up the case of HBV (B type hepatitis virus). The analytical items are specified depending on the type of the particle probe added after start of the operation. In the particle labeled probe solution container 90a, there is prepared beforehand a reagent having a single-stranded HBV-DNA probe having a magnetic latex particle fixed to its 3'-terminal and a fluorescent particle fixed to its 5'-terminal. The fluorescent particle is preferably a fluorescent latex particle containing a coumarin derivative serving as a fluorescent substance. The single-stranded HBV-DNA probe used was that having a complementary nucleotide sequence for the nucleic acid component to be analyzed.

As for the restriction enzyme solution, there is prepared beforehand, for example, Hae III as the restriction enzyme which cleaves double-stranded DNA formed by hybridizing the single-stranded HBV-DNA probe and the sample.

Upon start of the analyzing operation, into the reaction vessel 34 is pipetted the sample collected from the sample container 33 by the nozzle 43. Then, the latex particle reagent is collected from the particle labeled probe solution container 90a by the nozzle 43 and is dispensed into the reaction vessel 34. In this condition, HBV-DNA in the sample reacts with the single-stranded HBV-DNA probe having a magnetic latex particle fixed to its 3'-terminal and a fluorescent particle fixed to its 5'-terminal. The reaction vessel 34 is designed to maintain the reaction on the turntable 12 at a predetermined temperature (37° C.) for a predetermined period of time (15 minutes).

Then, with turn of the turntable 35, the restriction enzyme solution container 38a is brought to the suction position and a fixed amount of the solution containing the restriction enzyme Hae III 25 in the container 38a is sucked up by the pipetting nozzle 43 and pipetted into the corresponding reaction vessel 34 on the turntable 12. In the reaction vessel, the double-stranded DNA formed by hybridization between the single-stranded HBV-DNA probe combined with a latex particle and the nucleic acid component to be analyzed are cleft at predetermined cleavage locations. The fluorescent labeling latex particles are thereby liberated in the solution within the reaction vessel 34. A predetermined period of time (15 minutes) is also required for development of the liberating reaction.

Near the turntable 12, magnets are disposed in a particular region including the position of collecting the sample solution from one of the reaction vessels 34, as described above. When the reaction vessel 34 is transferred into the particular region, the magnetic latex particles cleft by the restriction enzyme and the unreacted magnetic latex particles are attracted to the wall of the reaction vessel under the action of the magnets, but the fluorescent labeling latex particles cleft by the restriction enzyme stay free in the solution. The sample solution containing those free particles is sucked at the sample solution collecting position by the pipetting nozzle 43 and dispensed into the sheath flow cell 47, whereby the number of the free particles is counted to determine a concentration of nucleic acids as the component to be analyzed.

FIG. 14 shows results of measuring four samples and one reagent blank in the form of a table. Of the sample numbers shown in the table, 1 to 4 represent samples taken from hepatitis patients and 5 represents the reagent blank.

The method of measuring nucleic acids according to the fifth embodiment of the present invention can also be carried out by using the above-described automatic analyzer similarly to the measuring method according to the first embodiment.

According to the present invention, as described hereinabove, nucleic acids can quickly be measured with high sensitivity without the need of washing and separating out a labeling substance in the unreacted reagent.

What is claimed is:

1. A reagent for detecting polynucleotides wherein said reagent contains polynucleotides each bound at 3'- and 5'-terminals thereof respectively with first and second particles.

2. A reagent used for detecting polynucleotides wherein said reagent contains polynucleotides each bound at 3'- and 5'-terminals thereof; with one terminal being labeled with a first binding moiety and the other terminal being labeled with a second binding moiety, and wherein first and second particles have specific binding partners for said first and second binding moieties and are bound to said first and second binding moieties respectively by said specific binding partners.

3. A reagent used for detecting polynucleotides wherein said reagent contains polynucleotides each bound at one of 3'- and 5'-terminals thereof with a binding moiety and at the other of the 3-' and 5'-terminals thereof with first particles, and said reagent including second particles each having a specific binding partner for said binding moiety.

4. A reagent used for detecting polynucleotides according to claim 1, wherein at least one of said first particle and said second particle is a particle having a label for detection.

5. A reagent used for detecting polynucleotides according to claim 1, wherein at least one of said first particle and said second particle is a light emitting particle.

6. A reagent used for detecting polynucleotides according to claim 5, wherein said light emitting particle is a fluorescent particle.

7. A reagent used for measuring nucleic acids wherein said reagent contains single stranded polynucleotides, each combined at one of 3' and 5'-terminals thereof with a particle having a label for detection and at the other terminal with a magnetic particle.

8. A reagent used for detecting polynucleotides wherein said reagent contains single stranded polynucleotide each combined at one of 3'- and 5'-terminals thereof with a particle having no label for detection and at the other terminal with a magnetic particle.

9. A method for detecting polynucleotides containing a specific polynucleotide sequence in a sample comprising:
(a) contacting a reagent with the sample under hybridizing conditions, wherein the reagent is a single stranded polynucleotide bound at the 3'- and 5'-terminals thereof with first and second particles respectively, and
(b) allowing said reagent to react with said polynucleotides in said sample to form double-stranded polynucleotides,
(c) cleaving double strands of said double-stranded polynucleotides,
(d) introducing a liquid containing two groups into a flow cell, one group being the first and second particles separated from each other by said cleaving and the other group being the first and second particles bound in any unreacted reagent from step (b),
(e) optically detecting to discriminate between the particles in both of said two groups and counting the number of particles in at least one of said two groups when said liquid flows through said flow cell, and
(f) measuring the presence of the polynucleotides containing the specific polynucleotide sequence in said sample based on said number of particles counted.

10. A method for detecting polynucleotide containing a specific polynucleotide sequence in a sample comprising:
(a) contacting a reagent with the sample under hybridizing conditions, wherein the reagent contains a single strand polynucleotide bound at the 3'- and 5'-terminals thereof with one terminal being labeled with a first binding moiety and the other terminal being labeled with a second binding moiety, respectively, and first and second particles bound by specific binding partners of said first and second binding moieties, and
(b) allowing said reagent, said particles and said polynucleotides in said sample to react to form double-stranded polynucleotides,
(c) cleaving double strands of said double-stranded polynucleotides,
(d) introducing a liquid containing two groups into a flow cell, one group being the first and the second particles separated from each other by said cleaving and the other group being the first and second particles bound in any unreacted reagent from step (b),
(e) optically detecting to discriminate between the particles in both of said two groups and counting the number of particles in at least one of said two groups when said liquid flows through said flow cell, and
(f) measuring the presence of the polynucleotides containing the specific polynucleotide sequence in said sample based on said number of particles counted.

11. A method for detecting polynucleotides containing a specific polynucleotide sequence in a sample comprising:
(a) contacting a reagent with the sample under hybridizing conditions, wherein the reagent contains a single strand polynucleotide bound at one of the 3'- and 5'-terminals thereof with a binding moiety and second particles bound with a specific binding partner for said binding moiety, and at the other of the 3'- and 5'-terminals thereof with a first particle;
(b) allowing said reagent and particle to react with said polynucleotides in said sample to form double-stranded polynucleotides,
(c) cleaving double strands of said double-stranded polynucleotides,
(d) introducing a liquid containing two groups into a flow cell, one group being the first and the second particles separated from each other by said cleaving and the other group being the first and second particles bound in any unreacted reagent from step (b),
(e) optically detecting to discriminate between the particles in both of said two groups and counting the number of particles in at least one of said two groups when said liquid flows through said flow cell, and
(f) measuring the presence of the polynucleotides containing the specific polynucleotide sequence in said sample based on said number of particles counted.

12. A method for detecting polynucleotides containing a specific polynucleotide sequence in a sample comprising:
(a) contacting a reagent with the sample under hybridizing conditions, wherein the reagent is a single stranded polynucleotide bound at one of the 3'- and 5'-terminals thereof with a particle having a label for detection and at the other of the 3'- and 5'-terminals thereof with a magnetic particle,
(b) allowing said reagent to react with said polynucleotides in said sample to form double-stranded polynucleotides,
(c) cleaving double strands of said double-stranded polynucleotides,
(d) attracting said magnetic particle by a magnet to separate magnetic particles from liberated labeled particles,
(e) introducing a liquid containing the liberated labeled particles into a flow cell,
(f) optically detecting and counting the number of said liberated labeled particles, when said liquid flows through said flow cell, and
(g) measuring the presence of the polynucleotides containing the specific polynucleotide sequence in said sample based on said number of labeled particles counted.

13. A method for detecting polynucleotides containing a specific polynucleotide sequence in a sample comprising:
(a) contacting a reagent with the sample under hybridizing conditions, wherein the reagent is a single stranded polynucleotide bound at one of the 3'- and 5'-terminals thereof with a particle having no label for detection and at the other one of the 3'- and 5'-terminals thereof with a magnetic particle, (b) allowing said reagent to react with said polynucleotides in said sample to form double-stranded polynucleotides, (c) cleaving double strands of said double-stranded polynucleotides, (d) attracting said magnetic particle by a magnet to separate magnetic particles from liberated unlabeled particles, (e) introducing a liquid containing the liberated unlabeled particles into a flow cell, (f) optically detecting and counting the number of said liberated unlabeled particles, when said liquid flows through said flow cell, and (g) measuring the presence of the polynucleotides containing the specific polynucleotide sequence in said sample based on said number of unlabeled particles counted.

14. A method for detecting polynucleotides according to claim 9 wherein said particles have a size of about 0.01 to about 10 μm.

15. A reagent for detecting polynucleotides according to claim 1 and wherein said particles have a size of about 0.01 to about 10 μm.

16. A method for detecting polynucleotides according to claim 9 wherein particles having different particle sizes are used as said first particle and said second particle, respectively.

17. A reagent for detecting polynucleotides according to claim 1 wherein said first particle and said second particle are particles having different particle sizes, respectively.

18. A method for detecting polynucleotides according to claim 9, wherein a particle having a label for detection is used as at least one of said first particles and said second particles.

19. A method for detecting polynucleotides according to claim 9, wherein a light emitting particle is used as at least one of said first particle and said second particle.

* * * * *